United States Patent [19]

Powell, Jr. et al.

[11] Patent Number: 4,861,584

[45] Date of Patent: Aug. 29, 1989

[54] ALLERGEN ABSORBENT AND BLOCKING AEROSOL COMPOSITION

[75] Inventors: Thomas W. Powell, Jr., Las Vegas, Nev.; Anthony A. Schulz, Floyds Knobs, Ind.; Gary W. Beall, Fairfield, Ky.

[73] Assignee: United Catalysts, Inc., Louisville, Ky.

[21] Appl. No.: 99,960

[22] Filed: Sep. 23, 1987

Related U.S. Application Data

[63] Continuation-in-part of Ser. No. 940,946, Dec. 12, 1986, abandoned, which is a continuation-in-part of Ser. No. 785,167, Oct. 7, 1985, abandoned.

[51] Int. Cl.$^4$ .................... A61K 31/14; A61K 31/74
[52] U.S. Cl. ........................ 424/79; 424/45; 514/642; 514/770; 514/862; 514/949
[58] Field of Search .............. 514/642, 770, 862, 949; 424/79, 45

[56] References Cited

U.S. PATENT DOCUMENTS

| | | | |
|---|---|---|---|
| 2,531,427 | 12/1950 | Hauser | 260/448 |
| 2,677,661 | 5/1954 | O'Halloran | 252/49.6 |
| 2,704,276 | 3/1955 | McCarthy et al. | 252/49.7 |
| 2,833,720 | 5/1958 | Stratton | 252/49.7 |
| 2,966,506 | 12/1960 | Jordan | 260/448 |
| 2,979,229 | 4/1961 | Reeder et al. | 221/22 |
| 3,252,757 | 5/1966 | Granquist | 23/111 |
| 3,294,683 | 12/1966 | Stansfield et al. | 252/28 |
| 3,568,394 | 3/1971 | Margolis | 53/21 |
| 3,586,478 | 6/1972 | Neumann | 23/111 |
| 3,666,407 | 5/1972 | Orlemann | 23/111 |
| 3,671,190 | 6/1972 | Neumann | 23/111 |
| 3,749,772 | 7/1973 | Cardarelli et al. | 424/81 |
| 3,835,896 | 9/1974 | Smrt | 141/3 |
| 3,844,978 | 10/1974 | Hickson | 252/455 R |
| 3,844,979 | 10/1974 | Hickson | 252/455 R |
| 3,852,405 | 12/1974 | Granquist | 423/118 |
| 3,855,147 | 12/1974 | Granquist | 252/317 |
| 3,857,422 | 12/1974 | Cunningham | 141/3 |
| 4,141,966 | 2/1979 | Willer et al. | 514/642 X |
| 4,380,505 | 4/1983 | Wittenhorst | 252/359 R |
| 4,412,018 | 10/1983 | Finlayson et al. | 523/508 |
| 4,450,095 | 5/1984 | Finlayson et al. | 252/315.2 |
| 4,497,823 | 2/1985 | Moore et al. | 514/862 X |
| 4,595,522 | 6/1986 | Bartlett | 252/305 |
| 4,659,571 | 4/1987 | Laba | 424/65 |

OTHER PUBLICATIONS

Handbook of Non Prescription Drugs, 5th ed., 1977, pp. 347–349.
Balsam et al., "Cosmetics, Science & Technology", 2nd ed., vol. 1, 1972, pp. 195–196.
Veitmeyer, N., Smithsonian, vol. 16(5) (1985).
Kligman, AMA Archives of Dermatology 77, 149 ff (Feb. 1958).
Majima, Ber. D. Chem. Ges. 40, 4390 (1907).
Majima, Ber. D. Chem. Ges. 50, 172 (1922).
McNair, J. Am. Chem. Soc. 43 159 (1921).
Hill et al., J. Am. Chem. Soc. 56, 2736 (1934).
Gosselin et al., Clinical Toxicology of Commercial Products, 5th Ed., Williams & Wilkens, 1984, p. 633.
Journal of the American College of Toxicology 1 (2), 71–83 (1982), "Final Report on the Safety Assessment of Quaternium-18 Hectorite and Quaternium-18 Bentonite".
Grim, R. E., Clay Mineralogy, 2nd Ed., McGraw-Hill Book Co., Inc., Chapter 10, "Clay-Mineral-Organic Reactions"; pp. 356–368, Ionic Reactions, Smectite; pp. 392–401, Organophilic Clay-Mineral Complexes.
Waali, E. E., "Testing Materials That Bond With Poison Oak/Ivy/Sumac Urushiol", Report prepared for U.S. Dept. of Agriculture Forest Service, Aug. 1983.

*Primary Examiner*—Leonard Schenkman
*Attorney, Agent, or Firm*—Vorys, Sater, Seymour and Pease

[57] ABSTRACT

An allergen absorbent and blocking aerosol composition for topical application to the skin comprises a highly activated organophilic clay of the smectite type, ion exchanged with a quaternary ammonium compound having aryl or alkyl groups in the range of from 10 to 22 carbon atoms, and a vehicle comprising one or more long-chain hydrocarbons or volatile silicone oils. The composition is preferably in the form of an aerosol composition additionally comprising an aerosol propellant. The composition is applied to the skin, preferably by spraying, to block and absorb the allergenic oils of toxic plants such as poison ivy and the like.

9 Claims, 2 Drawing Sheets

ALLERGEN ABSORBENT AND BLOCKING AEROSOL COMPOSITION

REFERENCE TO RELATED APPLICATIONS

This application is a continuation-in-part of copending application Serial No. 940,946, filed Dec. 12, 1986, now abandoned which is a continuation-in-part of, Ser. No. 785,167, filed Oct. 7, 1985, now abandoned.

BACKGROUND OF THE INVENTION

1. Field of the Invention

This invention relates to an allergen absorbent and blocking aerosol composition for topical application to the skin to prevent allergic skin reactions of persons due to contact with poison ivy, poison oak or poison sumac.

2. Description of the Prior Art

Poison ivy and poison oak are two of the major causes of allergic contact dermatitis in the United States today. According to Dr. William Epstein, as reported in the Smithsonian, Volume 16, Number 5, dated August, 1985 by Noel Vietmeyer:

"Poison ivy and oak are by far the major causes of allergic contact dermatitis in the United States. More people suffer from them than from all the other allergic skin diseases combined . . . No one counts the number of cases, but there are probably at least ten million a year, nationwide. Poison oak and poison ivy are possibly the greatest cause to workmen's disability in the nation; each year may bring more than 140,000 cases in the workplace, causing perhaps more than 152,000 lost work days."

According to Kligman *AMA Archives of Dermatology*, Vol. 77, February, 1958, p. 149, et seq., the first significant advance in Rhus biochemistry was made by Majima (Ber. Deutsch Chem. Ges. 40:4390, 1907 and 50:172, 1922), working with urushiol. Urushiol is a yellow oil extracted from the Japanese lac tree. Later, McNair (J. Am. Chem. Soc. 43:159, 1921), studied poison oak and concluded that the active principle (lobinol) was a catechol with an unsaturated side chain, whose position and structure were not identified. Hill and his collaborators (J. Am. Chem. Soc. 56:2736, 1934) later hydrogenated poison ivy urushiol. They obtained a product identical with Majima's hydrourushiol from Japanese lac. They therefore wrongly concluded that the antigenic compounds in the American and Japanese plants were identical.

According to Kligman, however:

"The sole chemical difference between Japanese lac and poison ivy is the position of one of the unsaturated bonds of the triolefin."

Strangely, however, the allergen urushiol does not appear to affect animals and household pets. Cats and dogs can be exposed and actually play in the area without being affected, but can infect their owners by brushing up against their skin and transferring the urushiol on their coats to the unexposed areas of the human anatomy. According to Dr. Epstein, Ibid.:

"Between 15 and 25% of us are essentially immune, 25% are mildly sensitive and don't normally develop severe reactions, 25 to 30% are moderately sensitive and break out significantly with the amount of urushiol found in one leaf and 10 to 20% are so exquisitely sensitive that less than one leaf produces intense dermatitis . . . "

The oily substance urushiol, when in contact with the skin, penetrates the outer skin layers and begins to chemically bind to the skin cells. The body sees the combination of the urushiol in chemical combination with a skin cell as a foreign intruder. The immune system immediately rushes large white cells called macrophages and T-lymphocytes to destroy the affected skin cells. Dr. Epstein explains, Ibid:

"It's the body's own over-reaction that causes the complications. In sensitized persons, the area fills up with the white blood cells and they release so much cell-destroying toxins that they tear apart even the skin itself. That's what produces the blisters and suppurating sores."

Many folk remedies have been proposed for use after contact with urushiol. These include morphine (topically), bromine, kerosene, gun powder, iodine, aqua regia, buttermilk, cream and marshmallows. Additionally, innumerable botanicals, such as snake root, coffee, gelisium, hellebore, ipecac, lobelia, mustard, opium, strychnine, veratrum, etc., have been suggested.

A major problem as to the contact with urushiol from poison oak, poison sumac and poison ivy is encountered by the foresters of the U.S. Forestry Service. This is particularly severe in the case of forest fires, where the soot and gases from the burning flames contain urushiol, which can get onto the foresters fighting the fire and even into their respiratory system. This is further complicated by the fact that the urushiol coats fomites, such as clothing, utensils, even carbon and soot in the area of forest fires and can therefore provide another method of contact, even outside the area of the plants themselves.

Prior to this invention, Dr. Edward E. Waali, working under contract with the U.S. Forestry Service, tested many materials in an effort to find a chemical which would absorb or somehow chenically bind urushiol. Waali tested solid absorbents, such as silica gel, alumina and activated charcoal. Additionally, he saturated samples of cloth and mordanted them with salts of aluminum, copper and chromium.

Dr. William L. Epstein, also working under contract with the U.S. Forestry Service, became aware of Dr. Waali's work and tested a wide variety of agents, including Sure® antiperspirant and Drysol™, both of which contain the antiperspirant aluminum chlorohydrate. The Sure® antiperspirant, in the spray form, contains aluminum chlorohydrate, cyclomethicone, quaternium-18 hectorite, perfume, ethanol, isobutane and propane. This composition is reported to contain from 1 to 5% quaternium-18 hectorite. See, for example, *Clinical Toxicology of Commercial Products*, Gosselin, et al, 5th edition, William and Watkins, 1984, PV-633.

Quaternium-18 hectorite is a reaction product of hectorite and quaternium-18 is commercially available as Bentone 38 (NL Chemicals). Quaternium-18 (CAS Number 61789-80-8) is predominantly (90 to 100%) a quaternary salt that conforms generally to the formula:

$$\left[ \begin{array}{c} CH_3 \\ | \\ R-N-R \\ | \\ CH_3 \end{array} \right]^+ Cl^-$$

where R represents hydrogenated tallow fatty radicals.

Quaternium-18, quaternium-18 hectorite and quaternium-18 bentonite are generally considered safe as cosmetic ingredients and have been widely used as suspending agents for antiperspirants. See "Final Report on the Safety Assessment of Quaternium-18, Quaternium-18 Hectorite, and Quaternium-18 Bentonite," *Journal of the American College of Toxicology*, Vol. 1(2), 1982, pp. 71–83.

Accordingly, a need has continued to exist for an effective and cosmetically acceptable material to protect humans from the effects of contact with poison ivy and similar poisonous plants.

SUMMARY OF THE INVENTION

This goal has now been achieved by an alllergen absorbent and blocking composition comprising a highly-activated organophilic clay gel and a long-chain hydrocarbon or volatile silicone fluid vehicle. The organophilic clay gel consists of layered platelets of smectite clay having a cation exchange capacity in excess of 50 milliequivalents per 100 grams of clay, which has been ion exchanged with a quaternary ammonium compound having at least one alkyl group containing from about 10 to 22 carbon atoms. It is essential that the smectite clay and quaternary ammonium compound be highly activated, and this is accomplished by high-shear mixing in a colloid mill or other known mechanisms. Additionally, low molecular weight polar activators, such as methanol, may be used.

According to this invention, the allergen absorbent and blocking composition is topically applied to the skin and clothes and thereby effectively blocks the skin and adjacent cloth from contact with urushiol and absorbs the urushiol and holds it away from the skin until it is washed off with soap and water. The highly-activated gel, consisting of platelets of the smectite clay, forms a barrier on the skin and clothes, possibly through contact of the active tallow tails of the organic material with the lipids of the skin and by absorption of the urushiol in the organic alkyl groups. It is felt, therefore, that there is a partitioning effect which effectively blocks and absorbs the oil phase urushiol from aqueous phase perspiration and the like, allowing the urushiol to be held away from the skin and held in chemical combination with the reactive alkyl chains of the organo-treated clay, while allowing the aqueous phase materials to pass through the clay barrier.

Accordingly, it is an object of the invention to provide a skin-protective composition.

A further object is to provide a protective composition capable of screening against poison ivy and the like.

A further object is to provide a composition which is effective for protecting skin from the effects of contact with poison ivy and which can be applied by spraying.

A further object is to provide an absorbent composition for urushiol.

Further objects of the invention will become apparent from the description of the invention which follows.

DETAILED DESCRIPTION OF THE INVENTION AND PREFERRED EMBODIMENTS

Figure 1:
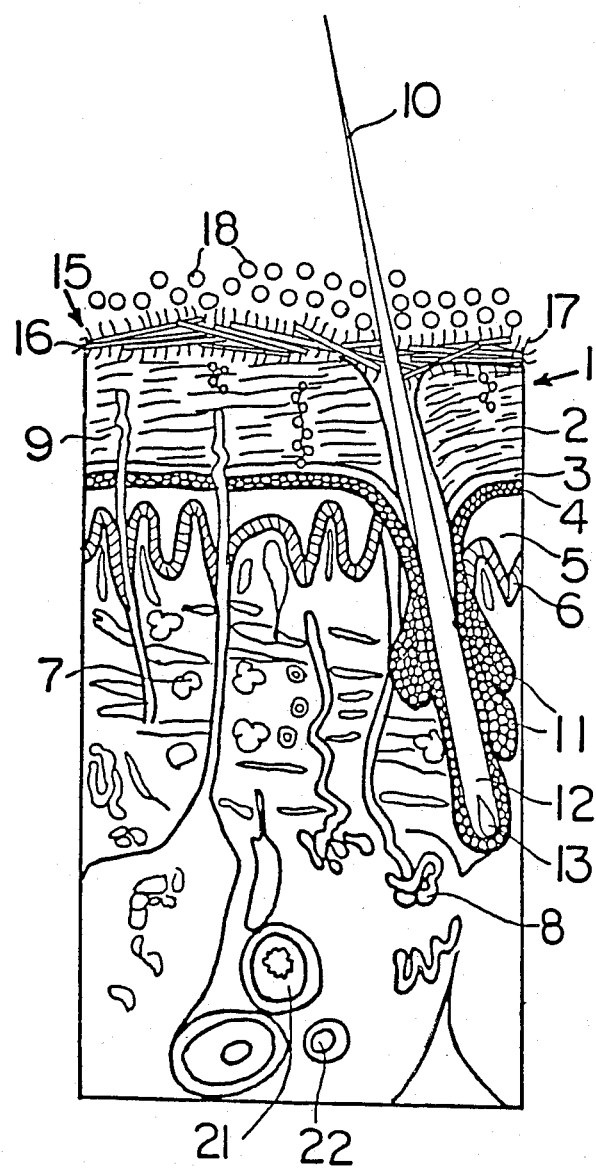
FIG. 1 is a diagrammatic view of the skin's surface and the organophilic clay platelets acting as a barrier to the invading urushiol droplets.

It has been known for a long time that organic compounds which contain a cation will react under favorable conditions by ion exchange with clay platelets which contain a negative layer-lattice and exchangeable cations to form organophilic organic-clay products. If the organic cation contains at least one alkyl group containing at least 10 carbon atoms, then such organoclays have the property of swelling in certain organic liquids. See, for example, U.S. Pat. No. 2,531,427 and U.S. Pat. No. 2,966,506, both of which are incorporated herein by reference. See also the book *Clay Mineralogy*, Second Edition, 1968, by Ralph E. Grim (McGraw-Hill Book Co., Inc.), particularly Chapter 10, "Clay-Mineral-Organic Reactions," pp. 356–368-"Ionic Reactions, Smectite;" and pp. 392–401-"Organophilic Clay-Mineral Complexes." Since the commercial introduction of these organo-clays in the early '50's, it has become well-known to gain maximum gelling (thickening) by adding a low molecular weight polar organic compound to the composition. Such polar organic compounds have been variously called activators, dispersion aids, solvating agents, and the like. See, for example, U.S. Pat. Nos. 2,677,661, O'Halloran; 2,704,276, McCarthy, et al; 2,833,720, Stratton; 2,979,229, Reeder et al.; and 3,294,683, Stansfield, et al, which are incorporated herein by reference. The most efficient and accepted polar materials for use as activators have been found to be low molecular weight alcohols and ketones, particularly methanol and acetone. The activators, however, have very low flash points and require the use of flame-proof apparatus. Higher-boiling activators, having higher flash points, such as propylene carbonate, may also be used. Clays used to prepare the allergen absorbent and blocking compositions of this invention are the smectite-type clays, having a high cation exchange capacity. The cation exchange capacity of the smectite clay should equal or exceed 50 milliequivalents per 100 grams of clay. The preferred range of milliequivalent capacity should be about 100–120 milliequivalents per 100 grams of clay. Particularly desirable types of clay are the naturally-occurring Wyoming variety of swelling bentonite and like clays, as well as hectorite, a swelling magnesium-lithium silicate clay. Suitable bentonite clays are also found in Europe, particularly in the Moosburg section of Bavaria. Smectite clays can be also prepared synthetically by either a pneumatolytic or preferably a hydrothermal synthesis process. Representative hydrothermal processes for preparing synthetic smectites are described in the following U.S. Patents, which processes are incorporated herein by reference: U.S. Pat. No. 3,252,757, Granquist; U.S. Pat. No. 3,586,478, Neumann; U.S. Pat. No. 3,666,407, Orelemann; U.S. Pat. No. 3,671,190, Neumann; U.S. Pat. No. 3,844,978, Hickson; U.S. Pat. No. 3,844,979, Hickson U.S. Pat. No. 3,852,405, Granquist; and U.S. Pat. No. 3,855,147; Granquist.

As has been previously indicated, the invention relates to the discovery that organo-treated clays of the smectite type, which are highly activated, produce allergen absorbents and blocking gels for topical application to the skin to prevent contact of the skin with the allergens produced by poison ivy, poison oak or poison sumac. The smectite-type clays, which have sufficient cation exchange capacity to be ion exchanged with organic compounds having a cation and one or more alkyl chains, having at least 10 carbon atoms naturally occur in Wyoming and in the Moosburg section of Bavaria, in the vicinity of Munich, Germany. The clays are of the bentonite type and are usually of the sodium form. However, if they are not already in the sodium form, they can be converted by passing an aqueous clay slurry through a bed of cation exchange resin in the sodium form. Alternately, the smectite clay can be mixed with water and a soluble sodium compound, such as sodium carbonate, or sodium hydroxide, and sheared at high shear in a colloid or pug mill or extruder. Representatives of such smectite clays are the following:

Montmorillonite:

$((Al_{4-x}Mg_x)Si_8O_{20}(OH)_{4-f}F_f) \cdot xR^+$ where $0.55 \leq X \leq 1.10$, $f \leq 4$ and R is selected from the group consisting of Na, Li, NH$_4$, and mixtures thereof;

Bentonite:

$((Al_{4-x}Mg_x)(Si_{8-y}Al_y)O_{20}(OH)_{4-f}F_f) \cdot (x+y)R^+$ where $10.0 \leq X \leq 1.10$, $0 \leq y \leq 1.10$, $0.55 \leq (x+y) \leq 1.10$, $f \leq 4$ and R is selected from the group consisting of Na, Li, NH$_4$, and mixtures thereof;

Beidellite:

$((Al_{4+y})(Si_{8-y}Al_y)O_{20}(OH)_{4-f}F_f) \cdot xR^+$, where $0.55 \leq X \leq 1.10$, $0 \leq y \leq 0.44$ and R is selected from the group consisting of Na, Li NH$_4$, and mixtures thereof;

Hectorite:

$((Mg_{6-x}Li_x)Si_8O_{20}(OH)_{4-f}F_f) \cdot xR^+$ where $0.57 \leq X \leq 1.15$, $f \leq 4$ and R is selected from the group consisting of Na, Li, NH$_4$, and mixtures thereof;

Saponite:

$((Mg_{6-y}Al_y)(Si_{8-x-y}Al_{x+y})O_{20}(OH)_{4-f}F_f) \cdot xR^+$ where $0.58 \leq X \leq 1.18$, $0 \leq y \leq 0.66$, $f \leq 4$ and R is selected from the group consisting of Na, Li, NH$_4$, and mixtures thereof;

Stevensite:

$((Mg_{6-x}Al_x)Si_8O_{20}(OH)_{4-f}F_f) \cdot 2xR^+$ where $0.28 \leq X \leq 0.57$, $f \leq 4$ and R is selected from the group consisting of Na, Li, NH$_4$, and mixtures thereof.

These smectite clays may be synthesized hydrothermally by forming an aqueous reaction mixture in the form of a slurry containing mixed hydrous oxides or hydroxides of the desired metals with or without, as the case may be, sodium (or alternate exchangeable cation or mixture thereof) fluoride in the proportions defined in the above formulas and preselected values of x, y, and f for the particular synthetic smectite desired. The slurry is then placed in an autoclave and heated under autogenous pressure to a temperature within the range of approximately 100° to 325° C., preferably 275° to 300° C. for a sufficient period of time to form the desired product. Formulation times of 3 to 48 hours are typical at 300° C., depending on the particular smectite being synthesized and the optimum time can be readily determined by pilot trials. The organic compounds useful in this invention are quaternary and ammonium salts containing at least one methyl radical and a mixture of alkyl radicals, having from 14 to 20 carbon atoms, preferably wherein 20 to 35% have 16 carbon atoms and 5% have 18 carbon atoms on a 100% basis. Additionally, quaternary ammonium compounds containing at least one methyl and one benzyl radical may be utilized. The anion is preferably selected from the group consisting of chloride and bromide and mixtures thereof and is preferably a chloride. However, other anions, such as acetate, hydroxide, nitrite, etc., may be present in the ammonium salt. The methyl or benzyl trialkyl ammonium salt may be represented as follows:

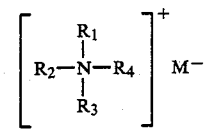

The preferred quaternary amine for use in the practice of this invention is dimethyl dihydrogenated tallow ammonium chloride. $R_1$ can be methyl or benzyl, $R_2$ can be methyl or $C_{10}$ to $C_{18}$. $R_3$ can be methyl or $C_{10}$ to $C_{18}$. $R_4$ can be $C_{10}$ to $C_{18}$. Commercially-prepared hydrogenated tallow typically analyzes 2.0% $C_{14}$, 0.5% $C_{15}$, 29.0% $C_{16}$, 1.5% $C_{17}$, 66.0% $C_{18}$ and 1.0% $C_{20}$ alkyl radicals.

Nevertheless, the alkyl radicals may be derived from other natural oils, including various vegetable oils, such as corn oil, soybean oil, cottonseed oil, castor oil and the like, as well as various animal oils and fats. Additionally, the alkyl radicals may be petrochemically derived, as from alpha olefins.

We hve found that is is essential that the organophilic clay compounds be highly activated. Activation of the organophilic clays may be accomplished by use of organic polar materials of low molecular weight (which are known as activators). These activators, dispersion aids and the like have previously been described.

PREPARATION OF THE ORGANOPHILIC CLAYS

The organophilic clays are prepared by admixing the smectite clay, the quaternary ammonium compound and water together, preferably at temperatures within the range of 100° to 171° F. (38° to 77° C.) for a period of time sufficient for the organic compound to coat the smectite clay platelets, followed by filtering, washing, drying and grinding. In using the organophilic clays in emulsions, the drying and grinding steps can be eliminated. When the smectite clay and quaternary ammonium compound and water are mixed together in such concentrations that a slurry is not formed, then the filtration and washing steps are eliminated. Preferably, however, the smectite clay is dispersed in water at a concentration of from about 3 to 7% and the slurry is optionally centrifuged to remove nonclay impurities. Thereafter, the slurry is agitated and heated to a temperature in the range of 140° to 171° F. (60° to 77° C.). The quaternary amine salt is added in the proper milliequivalent ration, preferably as a liquid in isopropanol. The amount of the quaternary ammonium salt added to the smectite clay for purposes of this invention must be sufficient to impart to the organo-philic clay the enhanced dispersion characteristics desired. Milliequivalent ratio is defined as the number of milliequivalents of the organic compound in the organo-clay per 100 grams of clay, on a 100% active clay basis. The organophilic clays preferably have a milliequivalent ration of from 100 to 120. A milliequivalent ratio of at least 50 is required to be effective. If polar organic activators are utilized, the lower milliequivalent ratios of 50 to 100 can be utilized without affecting the resultant gel system disadvantageously. The smectite clay and quaternary ammonium compound are admixed with known vehicles, as for example, long-chain hydrocarbons, such as isopropyl palmitate or isopropyl myristate, or volatile silicone vehicles, such as cyclomethicone or dimethicone or hexamethyldisiloxane. The entire admixture is subjected to a high-shear mixing in a colloid mill, a pug mill or the like. Generally speaking the concentration of the organo-treated clay is in the ratio of from 5 to 15% by weight. Therefore, the vechicle for the resulting gel makes up the balance of the mixture in the weight concentration of from about 95 to 85%.

If the gel is utilized in the form of an aerospray, the admixture of organo-treated clay forming the gel is in a weight concentration of from 5 to 15% and the hydrocarbon or silicone liquid vehicle forms the remaining 95 to 85%. The total gel makes up about 10 to 50% by weight of the contents of the can, with the rest of the material being a propellant.

AEROSOL PROPELLANTS

Aerosol propellants are well known in the art and have been described in some detail, as for example, in U.S. Pat. No. 3,835,896, to Smrt. Generally, with the banning of the chlorinated hydrocarbon propellants, the propellants used in the United States today are hydrocarbons. These are blends of isobutane and propane. According to Smrt:

"Isobutane is a colorless, easy-liquefiable gas which is generally shipped as a liquefield gas under its own vapor pressure. The vapor pressure of isobutane is 30.7 psig at 70° F. Propane is a gas at atmospheric pressure and normal temperatures and is colorless, both in its gaseous and liquid phases. Propane is also generally shipped as liquefied gas under its own vapor pressure, which is 110 psig at 70° F. The blends of hydrocarbon propellants are generally indentified by the vapor pressure of the blend at 70° F. Thus, for example, a 90-10 blend consists of 90% isobutane and 10% propane by weight and this blend has a pressure of 40 psig at 70° F. Blend 84-16 consists of 84% isobutane and 16% propane by weight and this blend has a vapor pressure of 46 psig at 70° F."

Therefore, the trade designation "A-46" relates to the vapor pressure of the propellant at 70° F.

Margolis goes further to state, in U.S. Pat. No. 3,568,394, that the low-boiling, liquefied alkanes, useful as propellants, are those which, alone or as mixtures at 70° F., have a vapor pressure of at least 20 pounds per square inch, but generally not more than 70 pounds per square inch. He lists alkanes, having vapor pressures in excess of 40 pounds per square inch as hexane, propane, pentane and butane. These, of course, can be mixed with alkanes having a lower vapor pressure to produce a desired pressure which is dependent upon the proportion of each of the specific alkanes present in the mixture. Such proportions are readily determined by methods which are well known to those skilled in the art.

Additionally, according to Bartlett, in U.S. Pat. No. 4,595,522, it is possible to utilize azeotropic mixtures of monochlorodifluoromethane and dimethyl ether in admixture with butane or isobutane to produce useful aerosol propellants with a vapor pressure in the range of 50 to 60 psig. Even noble gases, such as helium, neon, argon, krypton or mixtures thereof, have been proposed and have been used by some as propellants for an aerosol product. Thus, Wittenhorst, in 4,380,505, proposes their use so that the problems of chlorofluorohydrocarbon propellants are not encountered, since the noble gases do not apparently affect the ozone belt surrounding the earth.

AEROSOL FILLING

There are three different methods generally employed for filling assorted aerosol containers. These are described by Cunningham in U.S. Pat. No. 3,857,422, and are incorporated herein by reference. According to Cunningham, Column 1, lines 20 through 68 and Column 2, lines through 8:

"One is termed the "cold fill" method of filling. The product and liquefied propellant are individually refrigerated prior to their introduction into an open container. This refrigeration lowers the propellant vapor pressure so that it can be handled in the liquid state. This delays liquid to vapor transition of the propellant for a period sufficient to permit insertion and crimping of a valve assembly in the container to effect closure of the can. The cold fill method is not satisfactory for some products, due to the product formulation. For example, water base products freeze in the refrigeration step of the filling operation. Additionally, it has been found that some propellant is wasted in this type of filling operation in that some propellant will vaporize and escape from the container before closure of the container can be completed.

A second method employed for filling aerosol type containers is commonly referred to as the "under cap" method. In this operation, the product (at room temperature) is initially introduced into the container by a conventional liquid product filling machine and a valve is loosely inserted into the can. Generally, a vacuum is then drawn on the container, after which a liquid propellant is injected therein at high pressure (e.g., approximately 750 psig). Subsequently, the valve cup is crimped to the container by means of an internally expanding collet. However, in the time between the injection of the propellant into the container and the subsequent crimping operation, a portion of the liquid propellant is trapped between dual seals contacting the container and valve cup and around the curl of the can opening and valve cup over-lip. This propellant is lost in the filling operation. The loss of propellant for a single can is in excess of 5 grams . . . .

A third method employed for filling aerosol containers is known as "pressure filling." In this operation, the product is put into a container at room temperature, after which a valve assembly is inserted, a vacuum may be drawn, and the valve crimped. A propellant injector machine is then mated with the valve pedestal and propellant is supplied at high pressure and forced into the container through the valve assembly. The primary advantage of the pressure-filled method is a reduced loss of the propellant, as compared to either of the previously described methods of filling."

DESCRIPTION OF THE DRAWINGS

Referring now to FIG. 1, there is illustrated a diagrammatic section of the skin after a diagram of *Gray's Anatomy*. As will be noted, the skin is made up of an epidermis 1 and a dermis 7. The epidermis consists of five layers, the stratum corneum 2, the stratum lucideum 3, the stratum granulosum 4, the stratum mucosum 5, which terminates in the stratum germinationium 6. The sudoriferous gland 8 is located in the dermis. However, the ducts 9 extend through the epidermis to the outer layer of the skin. Additionally, the shaft of the hair 10 extends through duct 14 and terminates at the bulb 12. The hair follicle is surrounded by sebaceous glands 11, which discharge into the duct 14 to keep the hair shaft lubricated. Additionally, the dermis 7 contains a great deal of adipose tissue 20 and some relatively deep-lying arteries 21 and nerves 22.

Figure 2:
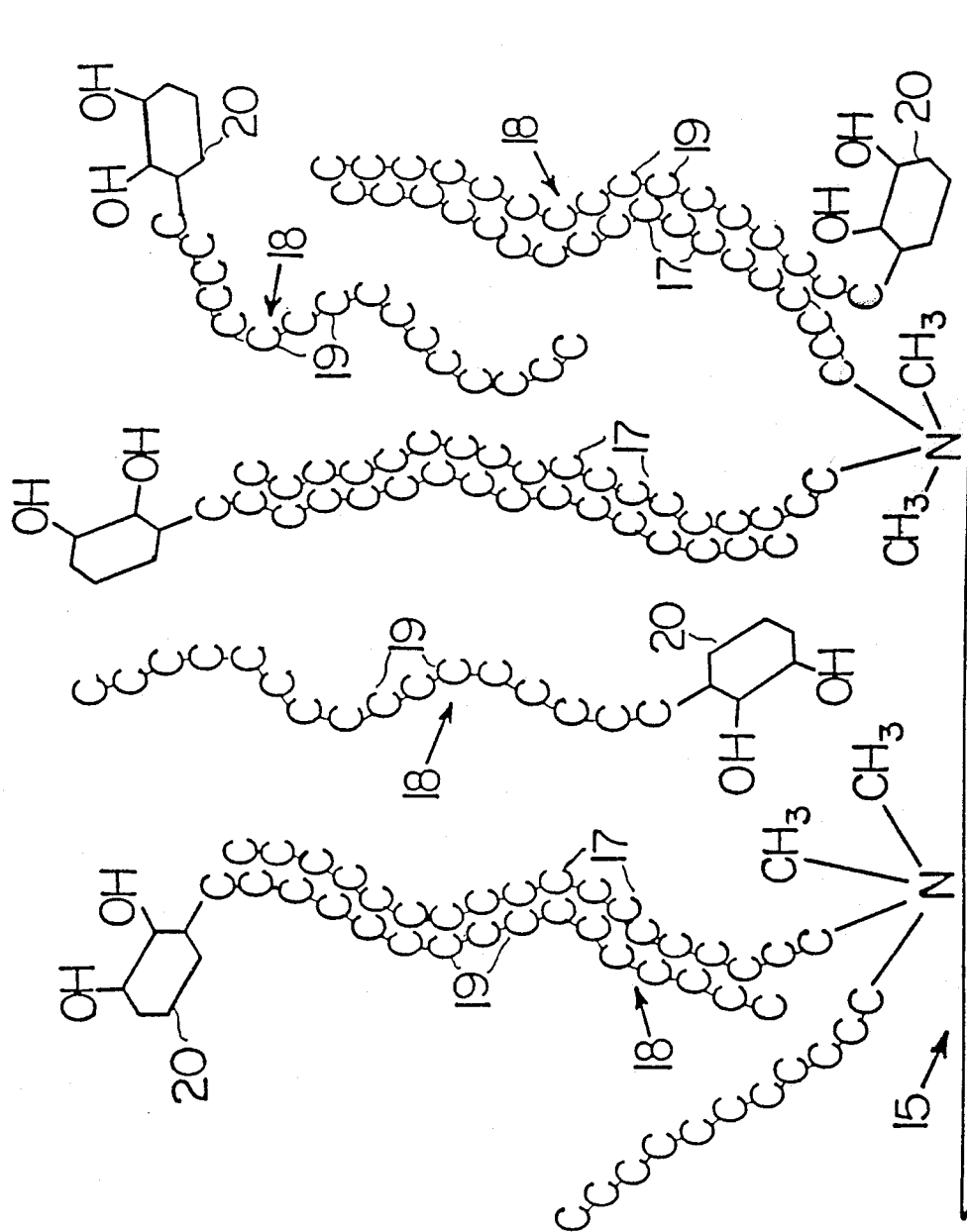
FIG. 2 is a diagrammatic view of an individual clay platelet with the alkyl groups attached thereto.

According to the drawing, the organo-treated clay 15, made up of platelets 16 and the depending tallow tails 17 form as a layer over the skin with the tallow tails reacting to some extent with the lipids of the skin's surface. This allows the platelets to align themselves to act somewhat as a shield against the invading urushiol droplets 18. Stroking of the platelets manually appears to orient the platelets so as to lie parallel with the epidermal cells of the skin. The quaternium bentonite or quaternium hectorite appears somewhat muddy when initially applied to the skin. However, as the quaternium-18 bentonite gel is stroked onto the skin, the muddy appearance disappears. The urushiol droplets, in order to reach the skin, must pass through the barriers or blockers formed by the platelets 16 without being absorbed by the reactive organic alkyl groups in the form of tallow tails 17. It is believed that the tallow tails, through the van-der Waal forces, tend to absorb chemically the urushiol droplets and hold the urushiol droplets and thus prevent their contact with the skin (see FIG. 2). Any urushiol droplets which might escape the first row of tallow tails are blocked by the clay platelets 16 and then encounter succeeding alkyl groups where absorption takes place. Additionally, the oragnophilic clay aerosol composition can be sprayed onto the clothes or tools, so as to suspend and inactivate the allergen until the clothes or tools can be laundered. Otherwise, there is some danger that other persons can be exposed to the allergen when these are laundered or that the worker himself may be reexposed by contact with the unwashed clothes at a later time.

Urushiol 18 is diagrammatically illustrated in FIG. 2, according to its chemical formula. As will be noted, the urushiol compound consists of a phenyl group 20 with two hydrogen groups and a long hydrocarbon chain of 15 to 17 carbons, designated as 19.

Additionally, the quaternary ammonium compounds are designated with the alkyl groups 17, consisting of 16 to 18 carbons. Some of the quaternary ammonium compounds contain a benzyl compound 21 and one alkyl chain and two methyl groups, while the other quaternary ammonium compounds consist of two alkyl hydrocarbon chains 17 and two methyl groups. The van der Waal bonding of the hydrocarbon chain 19 of the urushiol compound 18 is diagrammatically shown with the long-chain alkyl group 17 of the organophilic clay 15. Additionally, it is felt that the phenyl group 20 of the urushiol compound may have some affinity for the active surface of the platelet 16 of the organophilic clay. This is shown diagrammatically in the right-hand portion of FIG. 2.

It should be understood that this explanation is somewhat hypothetical. However, it is supported by data, as will hereinafter be shown. The fact of the matter is that absorption apparently is not the major mechanism in this instance, since materials with higher surface areas do not provide the protection that is provided by the organo-treated clays. It is felt, therefore, that the organic surface area is of major importance while the inorganic surface area formed by the pores of the clay platelets perform only a secondary function relative to the absorptive function performed by the reactive alkyl groups of the organic clays.

The invention will be better understood by reference to the following examples which are intended to be illustrative and not limiting.

EXAMPLE 1

A batch of organophilic clay is prepared by admixing finely milled sodium bentonite with sufficient quaternary ammonium compound so as to provide 85 milliequivalents of quaternary ammonium compound per 100 grams of clay. The quaternary ammonium compound is obtained from hydrogenated tallow and contains two alkyl groups containing from 16 to 18 carbons in length and 2 methyl groups. This is commonly referred to as quaternium-18. The quaternary ammonium compound was mixed with sufficient water and the sodium bentonite so as to produce a slurry containing about 4% by weight of clay. The temperature of the slurry was maintained at 170° for a period of about 30 minutes. This allowed the quaternary ammonium compound to ion exchange with the clay paticles. The slurry was then spray dried into a fine powder. This product is known in the cosmetic industry as quaternium-18 bentonite. The powdered organo-clay was admixed with about 4.3% by weight of an SD-40 alcohol and about 84% by weight of cyclomethicone (Dow-Corning 344) as a vehicle. This then produced a gel containing 11.3% organo-clay, 84% cyclomethicone and 4.3% SD-40 alcohol. The gel was then loaded into an aerosol container at room temperature. A valve assembly was inserted into the container and the valve was crimped. An A-46 mixed hydrocarbon propellant was then introduced through the valve assembly under pressure to produce an aerosol composition within the can of 30:70 weight ratio of gel to propellant. As previously mentioned, the A-46 propellant is 84% isobutane and 16% propane by weight and has a vapor pressure of 46 psig at 70%F.

EXAMPLE 2

The materials prepared as in Example 1 was tested for effectiveness in a procedure carried out under a grant from the U.S. Forestry Service under the supervision of Dr. William Epstein of the University of California Medical School at San Francisco. The test procedure involved the application of Sure® deodorant, as a comparison composition, and the organophilic clay of Example 1, by spraying onto the skin of the forearm, and subsequent challenge at 1, 4 and 24 hours after application by the application of dilutions of purified urushiol in acetone in a double-blind fashion. Three samples concentrations of urushiol in acetone were made up, with five microliter samples of the solution of urushiol in acetone containing amounts of urushiol ranging from 0.25 micrograms to 0.005 micrograms. The samples of urushiol in acetone were then applied to the patch test sites. The patch test sites were read two to five days later and recorded from N to 4 as follows:

N=Normal
1=Erythema and edema involving half the test
2=Erythema and edema plus small vesicles involving the entire site
3=Full involvement of the test site with erythema and edema and large vesicles
4=Bullae.

A−1 score signifies a definite positive reactive which involves less than ½ of the test site and a ± score signifies a questionable reaction which is subsequently read as either + or −.

The results of these tests are shown in Table I.

TABLE I

Average Protective Effect of SURE ® and Example I Compared to the Control

| Pretreatment Time | Microgram Dilutions of Urushiol | | | |
|---|---|---|---|---|
| | 0.25 | 0.1 | 0.05 | 0.025 |
| 1 hour | | | | |
| Sure ® | 1 | 1.3 | 1.2 | 1.0 |
| Example 1 | | Not Done | | |
| 4 hours | | | | |
| Sure ® | 1.5 | 0.9 | 0.9 | 0.5 |
| Example 1 | 3.0 | 2.0 | 1.8 | 1.3 |
| 24 hours | | | | |
| Sure ® | 0 | 0.75 | 1.0 | 0.4 |
| Example 1 | 1.5 | 0.9 | 0.9 | 1.5 |

Table I shows that pretreatment with the Sure ® deodorant does reduce the patch test reaction to dilutions of urushiol. However, Sure ® is not able to prevent the reactions completely, but simply reduce them. The material of Example 1, on the other hand, was more effective at reducing the reactions and this was particularly noticeable at 4 and 24 hours after applications, as compared to Sure ®. This table averages overall responses.

EXAMPLE 3

A second preliminary study was carried out, comparing the results of pretreatment with Sure ® to pretreatment with Drysol ™ (a 20% w/v concentrate of aluminum chloride hexahydrate in alcohol; a solution of aluminum chloride (hexahydrate) 20% w/v in anhydrous ethyl alcohol (S.D. alcohol) 93% v/v." *Physicians Desk Reference*, 36th Ed., 1982. Medical Economics Co., Inc., 1982). The pretreatment time was 4 hours. The patch tests were urushiol and the patch test readings were the same as described above.

This preliminary study, comparing the high concentration of the aluminum salt (Drysol ™) to Sure°, indicated that the alcoholic solution was less effective than Sure ®.

EXAMPLE 4

In the next series of experiments, the subjects were pretreated with breakdown products of Sure ® that either were missing the aluminum chlorohydrate or the suspending agents (hectorite and propylene carbonate). The patch tests with urushiol and the patch test readings were the same as described above.

These experiments compared the blocking effect of Sure ® with its ingredients, i.e. without fillers and without aluminum chlorohydrate. In one instance, Sure ® was compared to the aluminum compound containing preparation without the fillers, i.e. the quaternium-18 hectorite, and the two were equal on two occasions. Sure ® was more effective in one and definitely more effective in four instances. In no instance was the aluminum salt more effective than Sure ®. Sure ®, containing only the fillers and no aluminum, was compared to Sure ® and the two preparations were equal on two occasions. Sure ® was more effective than the filler preparations on two occasions and much more effective on one occasion. On the other hand, the filler was more effective than Sure ® on two occasions. Finally, in direct comparison of the filler versus the aluminum preparation, the filler was more effective than the aluminum salt on two occasions and much more effective in four additional trials. In one instance, the aluminum salt was more effective than the filler preparations.

EXAMPLE 5

The tests, as previously described, were carried out with three particularly sensitive individuals. These are shown in Tables II, III and IV.

As can be seen, after the second day, the control showed a normal reaction for the patch test for the low concentration, but a 2 reaction as to any concentration of urushiol above 0.05 micrograms. Sure ®, on the other hand, provided some protection at 0.05 micrograms and reduced the size of the reaction as to the concentration above 0.1. The material of Example 1, however, showed full protection 4 hours after application for all concentrations of the material. Essentially the same results were obtained after Day 4. Except with the control, the severity of the reactions increased. The severity of the reaction of the high concentration of urushiol increased with the Sure ® application, by the material of Example 1 gave full protection throughout the total range of concentration. Twenty-four hours after application, essentially the same results were obtained on Day 2. On Day 4, the severity of the reaction was greater with the control and with the Sure ® sample and there was a 1 range of reaction for the Example 1 after 24 hours.

TABLE II

| Micrograms Urushiol | Day 2 | | | Day 4 | | |
|---|---|---|---|---|---|---|
| | Control | Sure ® | Ex. 1 | Control | Sure ® | Ex. 1 |
| Urushiol applied 4 hours after application of protective composition: | | | | | | |
| 0.25 | 2 | −1 | N | 3 | 3 | N |
| 0.1 | 2 | 1 | N | 2 | 1 | N |
| 0.05 | 2 | N | N | 2 | N | N |
| 0.025 | N | N | N | N | N | N |
| 0.01 | N | N | N | N | N | N |
| Urushiol applied 24 hours after application or protective composition: | | | | | | |
| 0.25 | 2 | 1 | N | 3 | 3 | 1 |
| 0.1 | 2 | 1 | N | 2 | 1 | 1 |
| 0.05 | 2 | N | N | 2 | N | N |
| 0.025 | N | N | N | N | N | N |
| 0.01 | N | N | N | N | N | N |

TABLE III

| Micrograms Urushiol | Day 2 | | | Day 4 | | |
|---|---|---|---|---|---|---|
| | Control | Sure ® | Ex. 1 | Control | Sure ® | Ex. 1 |
| Urushiol applied 4 hours after application of protective composition: | | | | | | |
| 0.25 | 2 | 2 | N | 4 | 2 | N |
| 0.1 | 2 | 2 | N | 3 | 2 | N |
| 0.05 | 1 | −1 | N | 2 | 1 | N |
| 0.025 | −1 | N | N | N | N | N |
| Urushiol applied 24 hours after application or protective composition: | | | | | | |
| 0.25 | 2 | 2 | 2 | 4 | 2 | 2 |
| 0.1 | 2 | 2 | 2 | 3 | 2 | 2 |
| 0.05 | 1 | 1 | N | 2 | 1 | N |
| 0.025 | −1 | N | N | N | N | N |

TABLE IV

| Micrograms Urushiol | Day 2 | | | Day 4 | | |
|---|---|---|---|---|---|---|
| | Control | Sure ® | Ex. 1 | Control | Sure ® | Ex. 1 |
| Urushiol applied 4 hours after application of protective composition: | | | | | | |
| 0.05 | 2 | 2 | N | 3 | 2 | −1 |

TABLE IV-continued

| Micrograms Urushiol | Day 2 | | | Day 4 | | |
|---|---|---|---|---|---|---|
| | Control | Sure ® | Ex. 1 | Control | Sure ® | Ex. 1 |
| 0.025 | N | N | N | 1 | N | N |
| 0.01 | N | N | N | N | N | N |
| Urushiol applied 24 hours after application or protective composition: | | | | | | |
| 0.05 | 2 | 1 | 1 | 3 | 2 | 2 |
| 0.025 | N | −1 | N | 1 | N | N |
| 0.01 | N | N | N | N | N | N |

Table III, for a completely different individual, who was extremely sensitive, demonstrated a more severe reaction with both the control sample and the Sure ® sample, after Day 2 and Day 4, as compared to Table II. However, the quaternium-18 bentonite of Example 1 provided good protection, both for Day 2 and Day 4 throughout the entire range of urushiol concentrations. The severity of the reactions increased across the board after application and even the material of Example 1 showed a moderate grade 2 reaction for the higher concentrations on the second and fourth days. The superiority of the material of Example 1 over the control and over the Sure ® is shown, however, throughout.

Table IV demonstrates in like manner the protection afforded to the individual throughout a smaller range of urushiol concentrations. On the fourth day, when the urushiol was applied 4 hours after the protective composition, the material of Example 1 showed a positive reaction, as indicated by −1. In like manner, the table demonstrates that even when the urushiol is applied 24 hours after the protective composition there is protection against the low concentrations of urushiol by the organophilic clay of Example 1 on the second and fourth days following application.

A further series of tests was performed to compare the effectiveness of the composition of this invention with other compositions containing clays which have not been treated with a long-chain quaternary ammonium compound. Three compositions were prepared according to the procedures in the following Examples 6, 7 and 8.

EXAMPLE 6

An aerosol sample was prepared in the same manner as described in Example 1, except that only the cyclomethicone and alcohol were added to the aerosol can prior to charging with the A-46 mixed hydrocarbon propellant. The vehicle to propellent ratio, therefore, was 30:70. This sample did not contain any organo-clay in the form of quaternium-18 bentonite, and served as a control.

EXAMPLE 7

Another sample was prepared identically with the sample of Example 1, except that the sodium bentonite was not ion exchanged with a quaternary ammonium compound. Therefore, the the can contained a gel consisting of 11.3% bentonite (without the quaternary ammonium compound), 4.3% SD-40 alcohol and 84% cyclomethicone, and was pressure charged with the A-46 propellent in a weight ratio of 30:70, gel to propellant.

EXAMPLE 8

Example 8 was prepared in the identical method as Example 7, except that kaolin was substituted for the sodium bentonite. The composition, then, of the gel was 11.3% kaolin, 84% cyclomethicone and 4.3% alcohol. This gel was then charged with an A-46 propellant in a weight ratio of 30:70, gel to propellant.

These materials were tested as follows:

Screening:

Thirty-seven healthy male and female volunteers were screened with serial dilutions of purified urushiol in acetone and applied in 5 microliter aliquots ranging from 1.25 to 0.005 micrograms to determine their level of sensitivity and their end-point dilution. Of this group, 28 were entered into the test protocol.

Test method:

Subjects were randomly sprayed on the volar aspect of each forearm with one of the four test preparations of Examples 1, 6, 7 and 8, by a technician; 4 hours later the treated sites were exposed to 5 microliters of a solution of urushiol in acetone in 2 to 4 dilutions that clearly included the predetermined end-point dilution for each subject. The test sites were evaluated in 2 and 5 days and scored on a scale from 0 to 4 in which:

0 = no reaction
1 = erythema edema involving more than half the test area
2 = erythema, edema and small vesicles involving the full test area
3 = erythema, edema and significant vesiculation
4 = bullae Positive reactions that affected less than half the test area were scored as −1 and questionable reactions, usually seen on the first observation period, were scored ±. Subjects were tested every 10 to 14 days after the previous test sites had healed so that comparative, sequential data was obtained in a number of persons.

Results:

In this study, it was possible to analyze the data in two distinct ways. The first evaluation method consisted of a direct comparison of 2 preparations applied to the same subject on the same day. So long as at least one test site gave a positive reaction, the materials could be scored as better than or equal to each other on that single occasion. If both test sites were scored completely negative for poison ivy dermatitis, it was considered a null event and no comparison was recorded. The results of that evaluation are listed in Table V. It can be seen that there were 37 valid comparison events and that the composition of Example 1, according to the invention, on 16 occasions scored better than the compositions of Examples 6, 7, or 8; whereas on only one occasion did one of the compositions of Examples 6, 7 or 8 score better than the composition of Example 1. On the other hand, comparisons of the compositions of Examples 6, 7 and 8 amongst each other gave mixed results, so that none of those three preparations were seen to have a distinct advantage over the others.

The second evaluation method involved 16 subjects who were tested at least twice so that in most instances, all four materials, of Examples 1, 6, 7 and 8, were tested in the same subject but on different occasions. This data is presented in Table VI. Examination of this table indicates that all of the test substances (Examples 1, 6, 7 and 8) had some protective effect, and on some occasions, the effect was impressive. Nevertheless, a careful examination of this table indicates that preparation 1 always produced optimal protection, whereas the other preparations sometimes did but at other times did not.

It is clear that by both methods of evaluating the considerable amount of data obtained, that the composition of Example 1 is the most effective as a topical protection against experimental poison ivy dermatitis in this rather stringent test method which uses an acetone solution of purified urushiol. None of the compositions of the three Examples, 6, 7 and 8 can be distinguished as being more effective than the others. However, the composition of Example 1 is unquestionably superior to the compositions of Examples 6, 7 and 8 in the test system used.

TABLE V

Direct comparison of Topical Protective Effect

| Composition of Example | Number of Instances Superior to Composition of Example | | | |
|---|---|---|---|---|
| | 1 | 6 | 7 | 8 |
| 1 (invention) | — | 4 | 7 | 5 |
| 6 | 1 | — | 2 | 0/6 |
| 7 | 0 | 2 | — | 3 |
| 8 | 0 | 5/6 | 2 | — |

TABLE VI

| Subject | Pretreatment: Composition of Example | Amount of Urushiol (micrograms) | | | | | | | |
|---|---|---|---|---|---|---|---|---|---|
| | | 1.25 | 0.5 | 0.25 | 0.1 | 0.05 | 0.025 | 0.01 | 0.005 |
| #1 | 1 | | | | | | 0 | 0 | 0 |
| | 6 | | | | | | 1 | 0 | 0 |
| | 7 | | | | | | 2 | 0 | 0 |
| | 8 | | | | | | 2 | 1 | 0 |
| #2 | 1 | | | | | | | | |
| | 6 | 1 | ± | 0 | 0 | | | | |
| | 7 | 1 | 0 | 0 | 0 | | | | |
| | 8 | 1 | 0 | 0 | 0 | | | | |
| #3 | 1 | | | 0 | 0 | 0 | 0 | | |
| | 6 | | | 1 | −1 | 0 | 0 | | |
| | 7 | | | 0 | 0 | 0 | 0 | | |
| | 8 | | | 0 | 0 | 0 | 0 | | |
| #4 | 1 | 0 | 0 | 0 | 0 | | | | |
| | 6 | 2 | 1 | −1 | 0 | | | | |
| | 7 | 2-3 | −1 | −1 | 1 | | | | |
| | 8 | 0 | 0 | 0 | 0 | | | | |
| #5 | 1 | 0 | 0 | 0 | 0 | | | | |
| | 6 | 1 | 0 | 0 | 0 | | | | |
| | 7 | | | | | | | | |
| | 8 | −1 | 0 | 0 | 0 | | | | |
| #6 | 1 | | | | 0 | 0 | 0 | | |
| | 6 | | | | | | | | |
| | 7 | | | | 0 | 0 | 0 | | |
| | 8 | | | | 0 | 0 | 0 | | |
| #7 | 1 | | 1 | −1 | 0 | 0 | | | |
| | 6 | | 2 | 1 | 0 | 0 | | | |
| | 7 | | 0 | 0 | 0 | 0 | | | |
| | 8 | | 1 | 1 | 0 | 0 | | | |
| #8 | 1 | | 0 | 0 | 0 | 0 | | | |
| | 6 | | | | | | | | |
| | 7 | 1 | −1 | + | 0 | | | | |
| | 8 | −1 | + | 0 | 0 | | | | |
| #9 | 1 | | | | | | | | |
| | 6 | | | | | 1 | 0 | 0 | |
| | 7 | | | | | + | 0 | 0 | |
| | 8 | | | | | | | | |
| #10 | 1 | | | | 0 | 0 | 0 | 0 | |
| | 6 | | | | 2 | 0 | 0 | 0 | |
| | 7 | | | | 2 | 0 | 0 | 0 | |
| | 8 | | | | 1 | 0 | 0 | 0 | |
| #11 | 1 | | | | −1 | 0 | 0 | 0 | |
| | 6 | | | | 1 | + | 0 | 0 | |
| | 7 | | | | 1 | 0 | 0 | 0 | |
| | 8 | | | | 1-2 | −1 | 0 | 0 | |
| #12 | 1 | 0 | 0 | 0 | 0 | | | | |
| | 6 | 2 | 1 | −1 | 0 | | | | |
| | 7 | −1 | 0 | 0 | 0 | | | | |
| | 8 | 2 | 1 | −1 | 0 | | | | |
| #13 | 1 | | | 0 | 0 | 0 | 0 | | |
| | 6 | | | 2 | −1 | 0 | 0 | | |
| | 7 | | | 2 | −1 | + | 0 | | |
| | 8 | | | 2 | 1 | 0 | 0 | | |
| #14 | 1 | | | | 1 | 0 | 0 | 0 | 0 |
| | 6 | | | | 2 | 1-2 | 2 | 0 | |
| | 7 | | | | 3 | 2 | 2 | 1 | 0 |
| | 8 | | | | 2 | 2 | 1 | 0 | |
| #15 | 1 | | | | | 0 | 0 | | |
| | 6 | | | | | 0 | 0 | | |
| | 7 | | | | | 1 | 0 | | |
| | 8 | | | | | + | 0 | | |
| #16 | 1 | | 0 | 0 | 0 | 0 | | | |
| | 6 | | 1 | 2 | 0 | 0 | | | |
| | 7 | | 1 | 1 | −1 | 0 | | | |

TABLE VI-continued

| | | Amount of Urushiol (micrograms) | | | | | | | |
|---|---|---|---|---|---|---|---|---|---|
| Subject | Pretreatment: Composition of Example | 1.25 | 0.5 | 0.25 | 0.1 | 0.05 | 0.025 | 0.01 | 0.005 |
| | 8 | | 0 | 0 | 0 | 0 | | | |

It is believed that the long $C_{18}$ chain of the urushiol molecule is absorbed through alkyl groups of the organophilic smectite clays. Additionally, it is felt that the phenyl group of the urushiol may have some affinity for the active surface of the clay platelet itself. The material is preferably applied in aerosol from onto the skin and clothes, prior to encountering the urushiol-producing plants, such as poison ivy, oak or sumac. The comparative study, however, has clearly shown that the organophilic smectite clays of this invention are more effective than any material heretofore known in the prevention of experimentally-induced poison oak or ivy dermatitis.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:
1. A method of protecting the skin from contact with an allergen comprising applying to the skin of a subject in need thereof a barrier composition consisting essentially of
   (1) from about 5% to about 15% by weight of a smectite clay having an ion exchange capacity of at least 50 milliequivalents per 100 grams, said clay having been ion exchanged with at least 50 milliequivalents per 100 grams of said clay of a quaternary ammonium compound having at least one alkyl group containing more than 10 carbon atoms, and
   (2) from about 95% to about 85% by weight of a pharmaceutically acceptable non-toxic vehicle.
2. The method of claim 1 wherein said barrier composition further comprises a polar activator for said smectite clay in a proportion of from about 1% to about 4% by weight.
3. The method of claim 1 wherein said ion exchanged smectite clay is quaternium-18 bentonite.
4. The method of claim 1 wherein said ion exchanged smectite clay is quaternium-18 hectorite.
5. The method of claim 1 comprising the additional step of manually stroking the area of the skin to which said barrier composition has been applied, whereby platelets making up the structure of said clay are oriented to lie parallel with the surface of the skin.
6. The method of claim 1 wherein said barrier composition is applied by spraying.
7. The method of claim 1 wherein said barrier composition contains about 11.3% of said smectite clay.
8. A method of preventing contamination of clothes and utensils with an allergen comprising applying to said clothes and utensils a barrier composition consisting essentially of
   (1) from about 5% to about 15% by weight of a smectite clay having an ion exchange capacity of at least 50 milliequivalents per 100 grams, said clay having been ion exchanged with at least 50 milliequivalents per 100 grams of said clay of a quaternary ammonium compound having at least one alkyl group containing more than 10 carbon atoms, and
   (2) from about 95% to about 85% by weight of a pharmaceutically acceptable non-toxic vehicle.
9. The method of claim 8 wherein said barrier composition contains about 11.3% of said smectite clay.

* * * * *

UNITED STATES PATENT AND TRADEMARK OFFICE

CERTIFICATE EXTENDING PATENT TERM
UNDER 35 U.S.C. § 156

PATENT NO.    :  4,861,584

ISSUED        :  August 29, 1989

INVENTOR(S)   :  Thomas W. Powell, Jr. et al.

PATENT OWNER  :  United Catalysts, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,458 days from August 29, 2006, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 15th day of July 1998.

Bruce A. Lehman
Assistant Secretary of Commerce and
  Commissioner of Patents and Trademarks